US006533803B2

(12) United States Patent
Babaev

(10) Patent No.: US 6,533,803 B2
(45) Date of Patent: Mar. 18, 2003

(54) WOUND TREATMENT METHOD AND DEVICE WITH COMBINATION OF ULTRASOUND AND LASER ENERGY

(75) Inventor: Eilaz Babaev, Minnetonka, MN (US)

(73) Assignee: Advanced Medical Applications, Inc., Eden Prairie, MN (US)

(*) Notice: Subject to any disclaimer, the term of this patent is extended or adjusted under 35 U.S.C. 154(b) by 187 days.

(21) Appl. No.: 09/745,943

(22) Filed: Dec. 22, 2000

(65) Prior Publication Data

US 2002/0082666 A1 Jun. 27, 2002

(51) Int. Cl.[7] .............. A61B 18/18

(52) U.S. Cl. .............. 607/89; 606/10; 606/13; 604/20; 604/22; 601/2; 239/102.2

(58) Field of Search .............. 607/89, 88, 50, 607/81, 82, 100, 101, 1, 2; 239/102.2, 4, 102.1; 604/20, 21, 22; 601/2; 606/3, 9, 10, 13

(56) References Cited

U.S. PATENT DOCUMENTS 3,275,059 A 9/1966 McCullough
3,392,916 A 7/1968 Engstrom et al.
3,561,444 A 2/1971 Boucher
3,860,173 A 1/1975 Sata
4,052,004 A 10/1977 Martin et al.
4,085,893 A 4/1978 Durley, III
4,153,201 A 5/1979 Berger et al.
4,251,031 A 2/1981 Martin et al.
4,271,705 A 6/1981 Crostack
4,294,407 A 10/1981 Reichl et al.
4,301,093 A 11/1981 Eck
4,301,968 A 11/1981 Berger et al.
4,309,989 A 1/1982 Fahim
4,319,155 A 3/1982 Nakai et al.
4,334,531 A 6/1982 Reichl et al.
4,352,459 A 10/1982 Berger et al.
4,428,531 A 1/1984 Martin
4,466,571 A 8/1984 Muhlbauer
4,530,360 A 7/1985 Duarte
4,541,564 A 9/1985 Berger et al.
4,582,654 A 4/1986 Karnicky et al.
4,619,400 A 10/1986 Van Der Burgt
4,642,581 A 2/1987 Erickson
4,655,393 A 4/1987 Berger
4,659,014 A 4/1987 Soth et al.

(List continued on next page.)

FOREIGN PATENT DOCUMENTS

EP 0 156 4009 A2 2/1985
EP 0 437 155 B1 2/1990
EP 0 657 226 B1 11/1994
GB 2 099 710 A 12/1982
GB 2 101 500 A 1/1983
JP 2000237275 A2 9/2000
WO WO 96/35383 11/1996

OTHER PUBLICATIONS

Journal of Burn Care & Rehabilitation; vol. 21, No. 4; Jul./Aug. 2000 pp. 333–338.

(List continued on next page.)

*Primary Examiner*—Teresa Walberg
*Assistant Examiner*—Fadi H. Dahbour
(74) *Attorney, Agent, or Firm*—Carter, DeLuca, Farrell & Schmidt, LLP

(57) ABSTRACT

A method and device for wound treatment with a combination of laser and ultrasound waves comprises a probe to produce a laser beam and transducer to produce ultrasonic waves. The ultrasonic transducer has tip with a distal end comprising a radiation surface. A liquid is directed to the radiation surface wherein an directed atomized particle spray of the liquid is created upon contact of the liquid with the radiation surface. The laser beam and spray directed to the wound from at least 0.1 inches transmits ultrasound waves as well as particles and has an radiation, irrigation, mechanical cleansing, liquid energizing and bactericide effect on the wound.

24 Claims, 2 Drawing Sheets

U.S. PATENT DOCUMENTS

| | | | | | |
|---|---|---|---|---|---|
| 4,679,551 | A | | 7/1987 | Anthony | |
| 4,726,523 | A | | 2/1988 | Kokubo et al. | |
| 4,726,525 | A | | 2/1988 | Yonekawa et al. | |
| 4,733,820 | A | | 3/1988 | Endo et al. | |
| 4,756,478 | A | | 7/1988 | Endo et al. | |
| 4,783,003 | A | | 11/1988 | Hirabayashi et al. | |
| 4,790,479 | A | | 12/1988 | Matsumoto et al. | |
| 4,793,339 | A | | 12/1988 | Matsumoto et al. | |
| 4,850,534 | A | | 7/1989 | Takahashi et al. | |
| 4,877,989 | A | | 10/1989 | Drews et al. | |
| 4,905,671 | A | | 3/1990 | Senge et al. | |
| 4,930,700 | A | | 6/1990 | McKown | |
| 4,941,618 | A | | 7/1990 | Hildebrand et al. | |
| 4,961,885 | A | | 10/1990 | Avrahami et al. | |
| 5,002,059 | A | | 3/1991 | Crowley et al. | |
| 5,040,537 | A | | 8/1991 | Katakura | |
| 5,063,922 | A | | 11/1991 | Hakkinen | |
| 5,076,266 | A | | 12/1991 | Babeav | |
| 5,104,042 | A | | 4/1992 | McKown | |
| 5,115,805 | A | | 5/1992 | Bommannan et al. | |
| 5,134,993 | A | | 8/1992 | van der Linden et al. | |
| 5,163,433 | A | | 11/1992 | Kagawa et al. | |
| 5,172,692 | A | | 12/1992 | Kulow et al. | |
| 5,176,677 | A | * | 1/1993 | Wuchinich | 604/22 |
| 5,186,162 | A | | 2/1993 | Talish et al. | |
| 5,197,946 | A | | 3/1993 | Tachibana | |
| 5,211,160 | A | | 5/1993 | Talish et al. | |
| 5,231,975 | A | | 8/1993 | Bommannan et al. | |
| 5,269,291 | A | | 12/1993 | Carter | |
| 5,315,998 | A | | 5/1994 | Tachibana et al. | |
| 5,316,000 | A | | 5/1994 | Chapelon et al. | |
| 5,318,014 | A | | 6/1994 | Carter | |
| 5,323,769 | A | | 6/1994 | Bommannan et al. | |
| 5,324,255 | A | | 6/1994 | Passafaro et al. | |
| 5,334,183 | A | * | 8/1994 | Wuchinich | 604/22 |
| 5,345,940 | A | | 9/1994 | Seward et al. | |
| 5,347,998 | A | | 9/1994 | Hodson et al. | |
| 5,362,309 | A | | 11/1994 | Carter | |
| 5,374,266 | A | | 12/1994 | Kataoka et al. | |
| 5,380,411 | A | | 1/1995 | Schlief | |
| 5,393,296 | A | | 2/1995 | Rattner | |
| 5,437,606 | A | | 8/1995 | Tsukamoto | |
| 5,480,379 | A | * | 1/1996 | La Rosa | 604/22 |
| 5,515,841 | A | | 5/1996 | Robertson et al. | |
| 5,515,842 | A | | 5/1996 | Ramseyer et al. | |
| 5,516,043 | A | | 5/1996 | Manna et al. | |
| 5,520,166 | A | | 5/1996 | Ritson et al. | |
| 5,520,612 | A | | 5/1996 | Winder et al. | |
| 5,527,350 | A | | 6/1996 | Grove et al. | |
| 5,529,572 | A | | 6/1996 | Spector | |
| 5,545,124 | A | | 8/1996 | Krause et al. | |
| 5,551,416 | A | | 9/1996 | Stimpson et al. | |
| 5,554,172 | A | | 9/1996 | Horner et al. | |
| 5,556,372 | A | | 9/1996 | Talish et al. | |
| 5,562,609 | A | * | 10/1996 | Brumbach | 604/22 |
| 5,573,497 | A | | 11/1996 | Chapelon | |
| 5,616,140 | A | | 4/1997 | Prescott | |
| 5,626,554 | A | | 5/1997 | Ryaby et al. | |
| 5,643,179 | A | | 7/1997 | Fujimoto | |
| 5,656,016 | A | | 8/1997 | Ogden | |
| 5,658,323 | A | | 8/1997 | Miller | |
| 5,699,805 | A | | 12/1997 | Seward et al. | |
| 5,707,402 | A | | 1/1998 | Heim | |
| 5,707,403 | A | | 1/1998 | Grove et al. | |
| 5,730,705 | A | | 3/1998 | Talish et al. | |
| 5,735,811 | A | | 4/1998 | Brisken | |
| 5,743,863 | A | | 4/1998 | Chapelon | |
| 5,752,924 | A | | 5/1998 | Kaufman et al. | |
| 5,762,616 | A | | 6/1998 | Talish | |
| 5,785,972 | A | | 7/1998 | Tyler | |
| 5,835,678 | A | | 11/1998 | Li et al. | |
| 5,843,139 | A | | 12/1998 | Goedeke et al. | |
| 5,879,314 | A | | 3/1999 | Peterson et al. | |
| 5,879,364 | A | | 3/1999 | Bromfield et al. | |
| 5,882,302 | A | | 3/1999 | Driscoll, Jr. et al. | |
| 5,894,841 | A | | 4/1999 | Voges | |
| 5,947,921 | A | | 9/1999 | Johnson et al. | |
| 5,960,792 | A | | 10/1999 | Lloyd et al. | |
| 5,989,245 | A | | 11/1999 | Prescott | |
| 6,001,069 | A | | 12/1999 | Tachibana et al. | |
| 6,014,970 | A | | 1/2000 | Irvi et al. | |
| 6,024,718 | A | | 2/2000 | Chen et al. | |
| 6,026,808 | A | | 2/2000 | Armer et al. | |
| 6,027,495 | A | | 2/2000 | Miller | |
| 6,041,253 | A | | 3/2000 | Kost et al. | |
| 6,061,597 | A | | 5/2000 | Rieman et al. | |
| 6,076,519 | A | | 6/2000 | Johnson | |
| 6,083,159 | A | | 7/2000 | Driscoll, Jr. et al. | |
| 6,095,141 | A | | 8/2000 | Armer et al. | |
| 6,098,620 | A | | 8/2000 | Loyd et al. | |
| 6,102,298 | A | | 8/2000 | Bush et al. | |
| 6,106,547 | A | | 8/2000 | Huei-Jung | |
| 6,113,558 | A | | 9/2000 | Rosenschein et al. | |
| 6,113,570 | A | | 9/2000 | Siegel et al. | |
| 6,117,109 | A | * | 9/2000 | Eggers et al. | 604/22 |
| RE36,939 | E | | 10/2000 | Tachibana et al. | |
| 6,158,431 | A | | 12/2000 | Poole | |
| 6,162,211 | A | * | 12/2000 | Tankovich et al. | 606/9 |
| 6,176,839 | B1 | | 1/2001 | DeLuis et al. | |
| 6,186,963 | B1 | | 2/2001 | Schwarze et al. | |
| 6,190,315 | B1 | | 2/2001 | Kost et al. | |
| 6,190,336 | B1 | | 2/2001 | Duarte et al. | |
| 6,206,842 | B1 | | 3/2001 | Tu et al. | |
| 6,206,843 | B1 | | 3/2001 | Iger et al. | |
| 6,231,528 | B1 | | 5/2001 | Kaufman et al. | |
| 6,234,990 | B1 | | 5/2001 | Rowe et al. | |
| 6,251,099 | B1 | | 6/2001 | Kollias et al. | |
| 6,254,597 | B1 | * | 7/2001 | Rizoiu et al. | 606/13 |
| 6,267,771 | B1 | * | 7/2001 | Tankovich et al. | 606/9 |
| 6,273,864 | B1 | | 8/2001 | Duarte et al. | |
| 6,321,109 | B2 | | 11/2001 | Ben-Haim et al. | |
| 6,322,527 | B1 | | 11/2001 | Talish | |
| 6,325,769 | B1 | | 12/2001 | Klopotek | |
| 6,340,352 | B1 | * | 1/2002 | Okada et al. | 601/2 |
| 6,350,123 | B1 | * | 2/2002 | Rizoiu et al. | 606/10 |

OTHER PUBLICATIONS

Design and Application of Low–Frequency Ultrasound and Its Combination With Laser Radiation in Surgery and Therapy—Critical Reviews in Biomedical Engineering; 2001; pp. 502–519.

* cited by examiner

WOUND TREATMENT METHOD AND DEVICE WITH COMBINATION OF ULTRASOUND AND LASER ENERGY

FIELD OF INVENTION

The present invention relates to the treatment of wounds using ultrasound and laser energy. In particular, the present invention relates to a method of spraying liquid drugs to the wound surface using ultrasonic waves for delivering drugs, killing bacteria, cleansing a surface, and stimulating healthy tissue cells and treating wound with laser energy.

BACKGROUND OF THE INVENTION

Ultrasonic waves and laser beams have been widely used in medical applications, including diagnostics and therapy, as well as many industrial applications. Diagnostic use of ultrasound waves includes using ultrasonic waves to detect underlying structures in an object or human tissue. In this method, an ultrasonic transducer is placed in contact with the tissue (or object) via a coupling medium and high frequency (1–10 MHz) ultrasonic waves are directed into the tissue. Upon contact with the various underlying structures, the waves are reflected back to a receiver adjacent the transducer. By comparing the signals of the ultrasonic wave as sent with the reflected ultrasonic wave as received, an image of the underlying structure can be produced. This technique is particularly useful for identifying boundaries between components of tissue and can be used to detect irregular masses, tumors, and the like.

Three therapeutic medical uses of ultrasound waves include aerosol mist production, contact physiotherapy and soft tissue ablation. The ultrasound contact therapy procedure may cause a patient significant discomfort and/or pain and skin may appear raw and damaged. Aerosol mist production makes use of a nebulizer or inhaler to produce an aerosol mist for creating a humid environment and delivering drug to the lungs.

Ultrasonic nebulizers operate by the passage of ultrasound waves of sufficient intensity through a liquid, the waves being directed at an air-liquid interface of the liquid from a point underneath or within the liquid. Liquid particles are ejected from the surface of the liquid into the surrounding air following the disintegration of capillary waves produced by the ultrasound. This technique can produce a very fine dense fog or mist.

Aerosol mists produced by ultrasound are preferred because a smaller particle size of the aerosol can be obtained with the ultrasonic waves. One of the major shortcomings of ultrasonic inhalers and nebulizers is that there is no directed aerosol to the target. An air stream is then required to direct the aerosol to the target, but this decreases the efficiency of ultrasound.

Ultrasonic sprayers, produced by Sonic and Materials Inc., Misonix Inc., Sono-Tek Inc., Zevex International, Inc., and others, operate by passing liquid trough central orifice of an ultrasound instrument-tip. See, for example, U.S. Pat. Nos. 3,765,606, 4,659,014, 5,104,042, 4,9307,00, 4,153, 201, 4,655,393, 5,516,043, 5,835,678, 5,879,364, and 5,843, 139.

Ultrasonic inhalers and drug delivery systems from Medisonic USA, Inc., 3M, Siemens GmbH, The Procter & Gamble Company, Sheffield Pharmaceuticals, Aradigm, Inc., and others, operate by atomizing liquid using piezoceramic film. See, for example, U.S. Pat. Nos. 4,294,407, 5,347,998, 5,520,166, 5,960,792, 6,095,141, 6,102,298, 6,098,620, 6,026,808, and 6,106,547.

Medical usage of lasers can be divided in several groups: laser blood flow meters (Doppler), tissue ablation, therapy, revasculation and treatment devices, surgery devices, diagnostic devices, and others. Medical laser devices from HGM Medical Lasers Inc., Level Laser Medical Systems, Coherent, Inc., ESC Medical Systems, PLC Medical Systems, Inc., Palomar Medical, Altus Medical, Tissue Medical Lasers, Inc., and others, are appropriate for the therapy, dermatology, surgery, gynecology, urology, dentistry, veterinary, and other applications, operate by atomizing liquid using piezoceramic film. See, for example, U.S. Pat. Nos. 5,374,266, 5,527,350, 5,616,140, 5,707,403, 5,658,323, 6,027,495, and 5,989,245.

OBJECTS OF THE INVENTION

It is an object of the invention to provide an improved method and device for treating wounds.

It is also an object of this invention to provide an improved method and device for treating wounds using combination of different energy sources as ultrasound and laser.

It is a further object of the invention to provide a method and device for delivering drug, killing bacteria, cleansing a surface and stimulating healthy tissue cell growth.

It is a yet further object of the invention to treat a wound by spraying the surface of the wound with aerosol mist produced by ultrasonic waves and radiating by laser bearm.

These and other objects of the invention will become more apparent from the discussion below.

SUMMARY OF INVENTION

The present invention is a method and device using a combination of ultrasonic waves and laser beams to treat wounds. More particularly, the device of invention creates, directs and delivers ultrasound liquid aerosol spray and a laser beam to the wound surface for delivering drugs, killing bacteria, cleansing the surface, stimulating healthy tissue cells and treating the wound with ultrasound and laser energy. The method of the invention for treating wounds involves the use of a combination of a continuous or pulsed ultrasound waves and a beam of pulsed, scanned or gated continuous wave laser or incoherent radiation.

More particularly the method of the invention comprises producing a directed spray of liquid particles produced by contact of the liquid with a free end surface of an ultrasonic transducer, and the particle spray beam in combination with a laser beam are directed onto the wound. According to the method of the present invention a combination of ultrasonic waves, laser beams and energized medicines (highly activated by ultrasonic waves and laser beams) destroys the surface bacteria and results in a higher level of disinfection by the energized liquids as compared to ordinarily applied liquids. Additionally, the ultrasound and laser energy also stimulates healthy cell growth to aid in granulization and epithelization of healing tissue. Other applications of the method of the invention include non-medical uses such as cleansing, sterilizing and coating surfaces of objects and food with various agents.

The method of the present invention offers an approach that may re-establish use of some traditional antibiotics and presents a method for fighting bacteria without antibiotics when necessary. The effect of the method of the present invention in highly activating antibiotics may allow some traditional antibiotics to overcome bacteria which have become resistant to that antibiotic. Moreover, independent of the energizing effect on antibiotics, the ultrasonic waves and laser beams which are applied in the method of the present invention also directly physically destroy bacteria. This combined effect has been shown to significantly increase the healing of purulent infected wounds.

This method of wound treatment is particularly advantageous on wounds for which local topical application of a drug is desirable but contact with the wound must be avoided.

The method of the present invention also provides a system of non-contact drug delivery with combination of laser and ultrasound energy. Finally the wound treatment method is effective when applied to the surface whether the liquid sprayed is a drug, such as an antibiotic, antiseptic, or equivalent agent, oil, saline, water or a combination of any of the foregoing.

The overall concept of the present invention relates to a method and apparatus for wound treatment using a combination of different energy sources, such as a laser, ultrasound, electric current, magnetic field, ultraviolet, microwaves, radio frequency, and or equivalent sources, as will be apparent to one skilled in this art.

While the invention has been described in general terms, the construction and obvious advantages of the device and method of the present invention will be more clearly understood from the following description of the various specific embodiments when read in conjunction with the accompanying drawings.

DETAILED DESCRIPTION OF THE PREFERRED EMBODIMENTS

Figure 1:
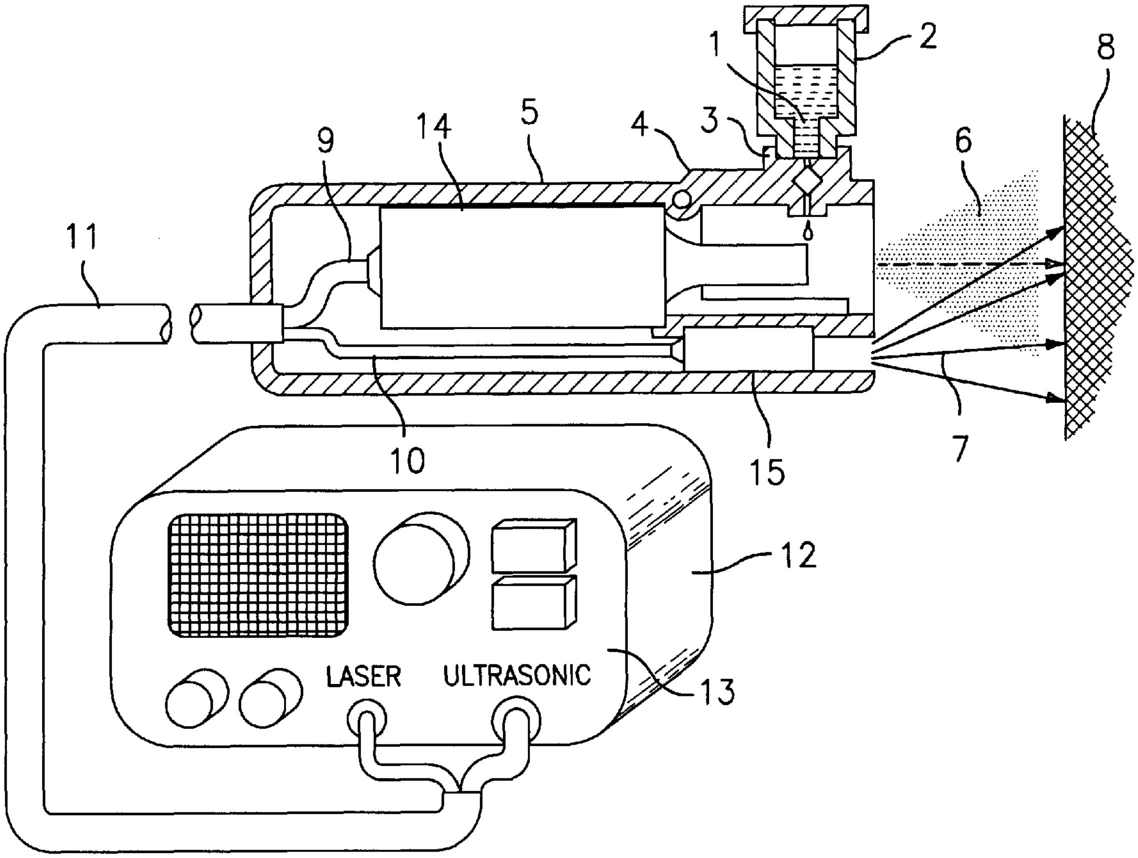
FIG. 1 is a schematic representation of a combined ultrasound and laser wound treatment system for use according to the present invention.

A device for wound treatment according to the present invention is illustrated in FIG. 1, which is a schematic representation of a side elevation of a preferred embodiment of the invention for wound treatment using ultrasound and laser energy. A body 12 has a front panel 13 having various regulatory controls, including on/off, display, intensity and others. Body 12 is connected to a handpiece 5 by an ultrasound cable 9 and a laser cable 10.

Handpiece 5 comprises a laser probe 15, an ultrasound transducer 14, and a liquid reservoir 2. Wound treatment solution 1 from a reservoir 2 is dispensed and delivered by valve 3 to contact the distal end of ultrasound transducer 14 and spray 6 onto the wound surface 8. At the same time, before or after laser source 15 has to be turned on and radiates the same wound surface 8. More detailed discussion of the operation of the ultrasound transducers can be found in commonly assigned, co-pending U.S. patent application Ser. No. 09/684,044, filed Oct. 6, 2000, and U.S. patent application Ser. No. 09/704,099, filed Nov. 1, 2000, both of which are incorporated herein by reference.

Figure 2A:
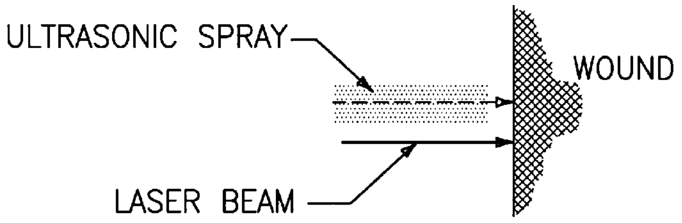
FIG. 2*a* is a schematic representation of a basic concept of the ultrasonic/laser device of the present invention, showing the ultrasonic spray and laser beams as mutually parallel.
Figure 2B:
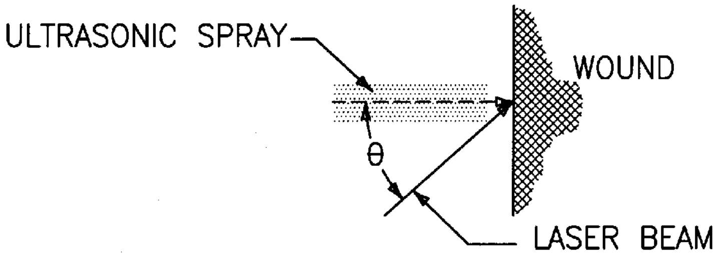
FIG. 2*b* is a schematic representation of a basic concept of the ultrasonic/laser device of the present invention showing the ultrasonic spray and laser beams as non-parallel.
Figure 2C:
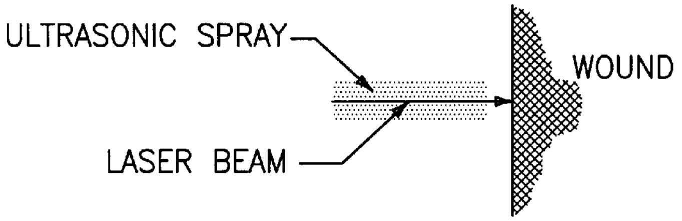
FIG. 2*c* is a schematic representation of a basic concept of the ultrasonic/laser device of the present invention showing the ultrasonic spray and laser beams as coaxial.

FIGS. 2*a*–2*c* illustrate the basic concept of ultrasound—laser treatment of a wound according to present invention. FIG. 2*a* is a schematic representation of the wound treatment method according to the present invention, where ultrasound spray and laser beam are directed to the wound in parallel. FIG. 2*b* is a schematic representation of the wound treatment method of the invention showing a coaxial-targeted ultrasound spray and laser beam. FIG. 2*c* is a schematic representation of the wound treatment according to the invention showing a targeted ultrasound spray and laser beam angle θ to each other.

Figure 3A:
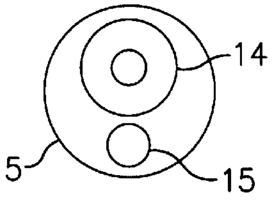
FIGS. 3*a*–3*d* are schematic representations of possible variations in the interaction of the laser beam and ultrasonic spray beam of the device depicted in FIG. 1.
Figure 3B:
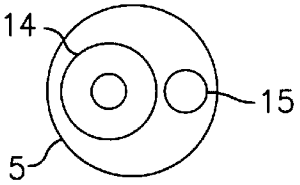
Figure 3C:
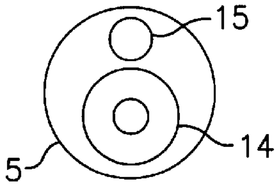
Figure 3D:
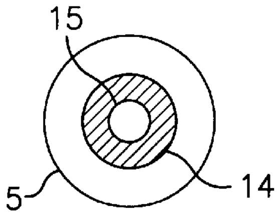

FIGS. 3*a*–3*d* depict schematic representations of possible locations of laser probe 15 and ultrasound transducer 14 relative to main body 5. The preferred location of the laser probe and the ultrasound transducer is shown in FIG. 3*a*, since it has been determined that this arrangement is most convenient, easy to handle and use. The alternative locations depicted in FIGS. 3*b*–3*d* may provide more convenient arrangements in certain applications, as will be apparent to one skilled in this art.

Laser radiation and spray sonication can be activated simultaneously or separately. The preferred treatment method is a simultaneous radiation and sonication procedure, since simultaneous treatment results in a doubling of laser and ultrasonic enhancement effect.

Main body 5 may or may not have disposable parts on the distal end to facilitate ease of use and sterilization.

It is provided that the ultrasound transducer 14 operates at a frequency from 18 kHz to 10,000 MHz. It is also provided that the liquid reservoir 2 is filled with one or more of the following components: antibiotics, antiseptics, saline, oil, and water. It is further provided that the free or distal end of the ultrasonic transducer 14 can be driven with a constant, modulated or pulsed frequency and that it is positioned at least 0.1 inch from the surface of the wound. It is also provided that the free or distal end can be driven with a sinusoidal, rectangular, trapezoidal or triangular wave form. Finally, it is provided that the laser beam can be coherent, pulsed, modulated, diverged (dispersed), converged (focused), and Q-switched.

The free or distal end of the ultrasonic transducer 14 can be modified by providing a thread, slot (groove), etc. The ultrasonic transducer 14 and the laser probe 15 can be housed together within one handpiece or separately within at least two handpieces.

While the preceding specific embodiments are illustrative of the practice of the invention, it will be understood by one skilled in this art that other expedients known to those skilled in the art or disclosed herein, may be employed without departing from the spirit of the invention or the scope of the appended claims.

What is claimed is:

1. A method for treating a wound using ultrasound and laser energy comprising the steps of:

providing an ultrasound transducer at a distance from the surface of the wound for emitting ultrasonic energy;

generating a spray by contacting a liquid with a portion of the ultrasound transducer;

providing a laser energy source at a distance from the surface of the wound for generating laser energy in the direction of the spray; and delivering the ultrasonic and laser energy to the wound through the spray, wherein the ultrasonic and laser energy penetrate the wound tissue to a beneficial depth to provide a bactericidal and a therapeutic effect for decreasing the healing time for the wound.

2. The method of claim 1, wherein the ultrasound transducer operates at a frequency of 18 kHz to $10^3$ MHz.

3. The method of claim 1, wherein the ultrasound transducer and the laser energy source are housed together within a single handpiece or separately within at least two handpieces.

4. The method of claim 1, further comprising the step of positioning the handpiece at a distance of at least 0.1 inch from the surface of the wound.

5. The method of claim 1, further comprising the step of energizing liquid particles of the spray by at least one of the ultrasonic energy and laser energy.

6. The method of claim 1, wherein the step of delivering the ultrasonic and laser energy comprises the step of delivering the ultrasonic and laser energy either simultaneously or separately.

7. The method of claim 1, further comprising the step of driving the ultrasound transducer by a signal having at least one of a constant, pulsed and modulated frequency.

8. The method of claim 1, further comprising the step of driving the ultrasound transducer using a wave form selected from the group consisting of sinusoidal, rectangular, trapezoidal and triangular wave forms.

9. The method of claim 1, wherein the portion of the ultrasound transducer includes at least one of a thread and a slot.

10. The method of claim 1, wherein the laser energy source generates the laser energy in the form of a laser beam, and wherein the laser beam is at least one of a coherent, pulsed, modulated, diverged, converged, and Q-switched laser beam.

11. The method of claim 1, wherein the therapeutic effect is selected from the group consisting of increasing blood flow to the wound, mechanically cleansing the wound, stimulating cell growth, providing at least one medicament to the wound, and penetrating at least one medicament through the surface of the wound.

12. The method of claim 1, wherein the liquid includes one or more components selected from the group consisting of antibiotics, antiseptics, saline, oil, and water.

13. The method of claim 1, wherein the spray is directed along a first direction and the laser energy is directed along a second direction, wherein the first and second directions are one of parallel, coaxial and at an angle with respect to each other.

14. An apparatus for treating a wound using ultrasound and laser energy comprising:

means for generating ultrasonic energy positioned at a non-contact distance from the surface of the wound;

means for introducing a liquid to the means for generating ultrasonic energy to generate a spray; and means for generating laser energy in the direction of the spray and at a non-contact distance from the surface of the wound, wherein the ultrasonic and laser energy are delivered to the wound through the spray, and wherein the ultrasonic and laser energy penetrate the wound tissue to a beneficial depth to provide a bactericidal and a therapeutic effect for decreasing the healing time for the wound.

15. The apparatus of claim 14, wherein the means for generating ultrasonic energy operates at a frequency of 18 kHz to $10^3$ MHz.

16. The apparatus of claim 14, wherein the means for generating ultrasonic energy and the means for generating laser energy are housed together within a single handpiece or separately within at least two handpieces.

17. The apparatus of claim 14, wherein the non-contact distance is at least 0.1 inch from the surface of the wound.

18. The apparatus of claim 14, wherein the ultrasonic and laser energy are delivered either simultaneously or separately.

19. The apparatus of claim 14, wherein the means for generating ultrasonic energy is driven by a signal having at least one of a constant, pulsed and modulated frequency.

20. The apparatus of claim 14, wherein the means for generating ultrasonic energy is driven by a signal having a wave form selected from the group consisting of sinusoidal, rectangular, trapezoidal and triangular wave forms.

21. The apparatus of claim 14, wherein the means for generating laser energy generates laser energy in the form of a laser beam, and wherein the laser beam is at least one of a coherent, pulsed, modulated, diverged, converged, and Q-switched laser beam.

22. The apparatus of claim 14, wherein the therapeutic effect is selected from the group consisting of increasing blood flow to the wound, mechanically cleansing the wound, stimulating cell growth, providing at least one medicament to the wound, and penetrating at least one medicament through the surface of the wound.

23. The apparatus of claim 14, wherein the liquid includes one or more components selected from the group consisting of antibiotics, antiseptics, saline, oil, and water.

24. The apparatus of claim 14, wherein the spray is directed along a first direction and the laser energy is directed along a second direction, wherein the first and second directions are one of parallel, coaxial and at an angle with respect to each other.

* * * * *